US010107620B2

(12) United States Patent
Miyazaki

(10) Patent No.: US 10,107,620 B2
(45) Date of Patent: Oct. 23, 2018

(54) IMAGE PICKUP APPARATUS

(71) Applicant: OLYMPUS CORPORATION, Hachioji-shi, Tokyo (JP)

(72) Inventor: Kanto Miyazaki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/434,589

(22) Filed: Feb. 16, 2017

(65) Prior Publication Data

US 2017/0160076 A1 Jun. 8, 2017

Related U.S. Application Data

(63) Continuation of application No. PCT/JP2014/004517, filed on Sep. 3, 2014.

(51) Int. Cl.
G01J 1/58 (2006.01)
G01B 11/24 (2006.01)
H04N 13/229 (2018.01)
G01N 21/64 (2006.01)
G02B 21/16 (2006.01)
(Continued)

(52) U.S. Cl.
CPC ......... G01B 11/24 (2013.01); G01N 21/6458 (2013.01); G02B 21/16 (2013.01); G02B 21/18 (2013.01); G02B 21/22 (2013.01); G02B 21/361 (2013.01); G02B 21/367 (2013.01);
(Continued)

(58) Field of Classification Search
CPC ........... G01N 21/6428; G01N 21/6458; G01N 21/6408; G01N 21/645; G01N 21/6452
See application file for complete search history.

(56) References Cited

U.S. PATENT DOCUMENTS 5,214,581 A * 5/1993 Rhodes .................... G03H 5/00
378/7
6,674,574 B1 * 1/2004 Aono ................... G02B 21/025
250/201.3
(Continued)

FOREIGN PATENT DOCUMENTS

JP 2000089124 A 3/2000
JP 2002344800 A 11/2002
(Continued)

OTHER PUBLICATIONS

International Search Report (ISR) and Written Opinion dated Dec. 2, 2014 issued in International Application No. PCT/JP2014/004517.
(Continued)

Primary Examiner — Edwin Gunberg
Assistant Examiner — Mamadou Faye
(74) Attorney, Agent, or Firm — Holtz, Holtz & Volek PC

(57) ABSTRACT

An image pickup apparatus includes observation units that observe an object from different directions and an image processor. Each of the observation units includes an objective lens, a lens array, and an image pickup element, receives light with the image pickup element, the light being modulated by the object and passing through the objective lens and the lens array, and outputs image signals having a phase difference. The image processor measures a shape of the object in terms of the relative distance from a reference point based on the image signals from the observation units.

7 Claims, 12 Drawing Sheets

(51) Int. Cl.
| | |
|---|---|
| *G02B 21/36* | (2006.01) |
| *G02B 21/18* | (2006.01) |
| *G02B 21/22* | (2006.01) |
| *H04N 13/232* | (2018.01) |
| *G02B 21/14* | (2006.01) |

(52) U.S. Cl.
CPC ......... *H04N 13/229* (2018.05); *H04N 13/232* (2018.05); *G02B 21/14* (2013.01)

(56) References Cited

U.S. PATENT DOCUMENTS

| | | | |
|---|---|---|---|
| 6,885,460 B2* | 4/2005 | Morita | G01B 11/2441 356/514 |
| 8,274,040 B2* | 9/2012 | Zhong | G01N 21/648 250/239 |
| 2005/0033420 A1* | 2/2005 | Christie | A61B 3/152 623/5.12 |
| 2005/0237604 A1 | 10/2005 | Kawano et al. | |
| 2010/0188739 A1 | 7/2010 | Watson | |

FOREIGN PATENT DOCUMENTS

| | | |
|---|---|---|
| JP | 2005300665 A | 10/2005 |
| JP | 2012163910 A | 8/2012 |
| JP | 2013517510 A | 5/2013 |
| JP | 2014116789 A | 6/2014 |

OTHER PUBLICATIONS

Japanese Office Action dated Jun. 12, 2018 (and English language translation thereof) issued in counterpart Japanese Application No. 2016-546196.

\* cited by examiner

US 10,107,620 B2

IMAGE PICKUP APPARATUS

CROSS-REFERENCE TO RELATED APPLICATION

The present application is a Continuing Application based on International Application PCT/JP2014/004517 filed on Sep. 3, 2014, the entire disclosure of which is incorporated herein by reference.

TECHNICAL FIELD

This disclosure relates to an image pickup apparatus.

BACKGROUND

JP 2012-163910 A (PTL 1) discloses a microscope apparatus that, by applying a light field technique, can measure the stereoscopic shape of a specimen from a parallax image.

CITATION LIST

Patent Literature

PTL 1: JP 2012-163910 A

SUMMARY

The microscope apparatus disclosed in PTL 1 is provided with one observation optical system and is configured to measure a stereoscopic shape in one direction of a specimen. Therefore, when measuring a stereoscopic shape in a different direction of the specimen, the specimen needs to be rotated relative to the one observation optical system. Measurements thus take time. Furthermore, depending on the specimen, it may not be possible to measure the stereoscopic shape accurately, since the shape may change over time, or the shape may change due to the effect of gravity upon rotating the specimen.

It would therefore be helpful to provide an image pickup apparatus that allows rapid acquisition of accurate stereoscopic shape information on an object.

An image pickup apparatus according to this disclosure includes:

a plurality of observation units configured to observe an object from different directions; and an image processor:

such that each of the plurality of observation units comprises an objective lens, a lens array, and an image pickup element, receives light with the image pickup element, the light being modulated by the object and passing through the objective lens and the lens array, and outputs a plurality of image signals having a phase difference; and such that the image processor measures a shape of the object in terms of relative distance from a reference point based on the image signals from the plurality of observation units.

The lens array may be disposed at a formation position of an image of the object; and the image pickup element may be disposed at a focal position of the lens array.

The lens array may be disposed so as to form an image of the object again; and the image pickup element may be disposed at a position where the image of the object is formed again by the lens array.

For each of the plurality of observation units, a focal position on an object side of the objective lens may be positioned at the reference point.

The image pickup apparatus may further include a projector configured to project a marker that becomes the reference point.

The projector may project the marker through the objective lens of one observation unit among the plurality of observation units onto the focal position on the object side of the objective lens.

The reference point may be set using a scatterer disposed in an observation area.

The plurality of observation units may measure the shape by fluorescent observation of the object.

According to this disclosure, an image pickup apparatus that allows rapid acquisition of accurate stereoscopic shape information on an object can be provided.

DETAILED DESCRIPTION

The following describes embodiments with reference to the drawings.

Embodiment 1

Figure 1:
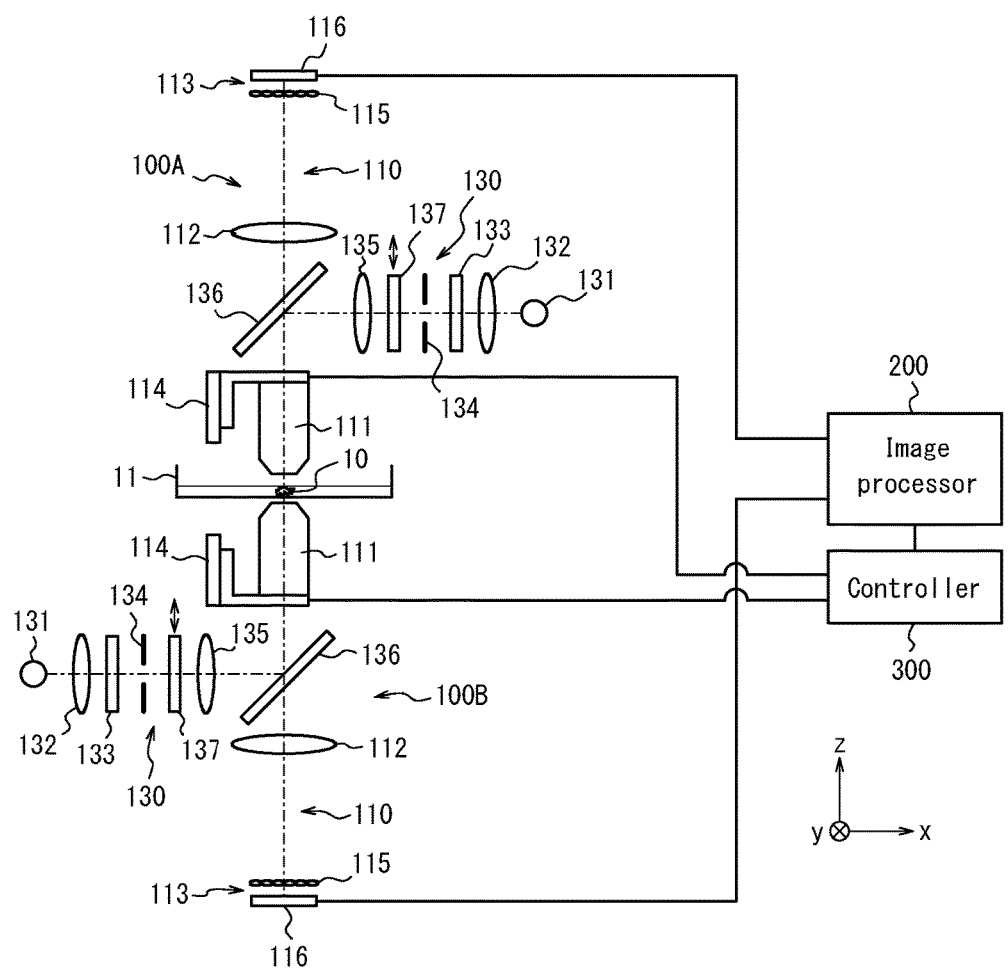
FIG. 1 schematically illustrates the main structure of a microscope apparatus as an image pickup apparatus according to Embodiment 1.

FIG. 1 schematically illustrates the main structure of a microscope apparatus as an image pickup apparatus according to Embodiment 1. The microscope apparatus according to this embodiment includes an observation unit 100A that observes the upper portion of a specimen (object) 10, an observation unit 100B that observes the lower portion of the specimen 10, an image processor 200, and a controller 300 that controls overall operations of the microscope apparatus. In FIG. 1, for the sake of explanation, the optical axis direction of the observation unit 100A is defined as the z-axis direction; the direction within the page, orthogonal to the z-axis direction, is defined as the x-axis direction; and the direction perpendicular to the page, orthogonal to both the z-axis direction and the x-axis direction, is defined as the y-axis direction.

The observation unit 100A includes an observation optical system 110 and a reflected illumination optical system 130. The observation optical system 110 includes an objective lens 111, an imaging lens 112, and a camera portion 113. The area between the objective lens 111 and the imaging lens 112 is a so-called infinity-corrected optical system, in which light beams from an in-focus specimen are collimated. The focus adjustment is either made manually or made automatically by the controller 300, by moving either the entire observation unit 100A or only the objective lens 111 in the optical axis direction of the objective lens 111 via a fine focus mechanism 114. The amount of movement at that time is read by a movement amount detector, such as a linear scale, provided in the fine focus mechanism 114 and is stored in the controller 300.

The camera portion 113 forms a light field camera and includes a microlens array 115 and an image pickup element 116. FIG. 1 illustrates an example of a so-called Plenoptic 1.0 type configuration, in which the microlens array 115 is disposed at the image-side focal position of the imaging lens 112, and the image pickup element 116 is disposed at the focal position of the microlens array 115.

Figure 2A:
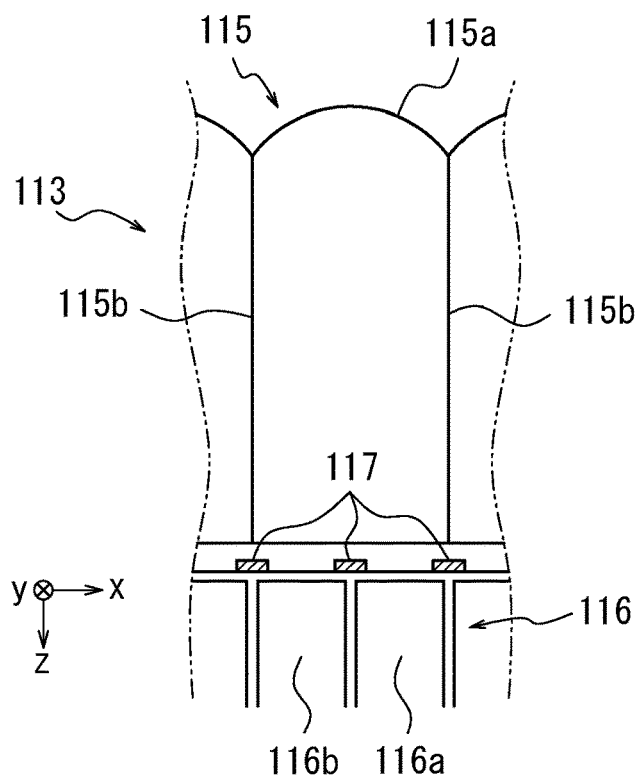
FIG. 2A is a partially expanded cross-sectional diagram of the camera portion in FIG. 1.
Figure 2B:
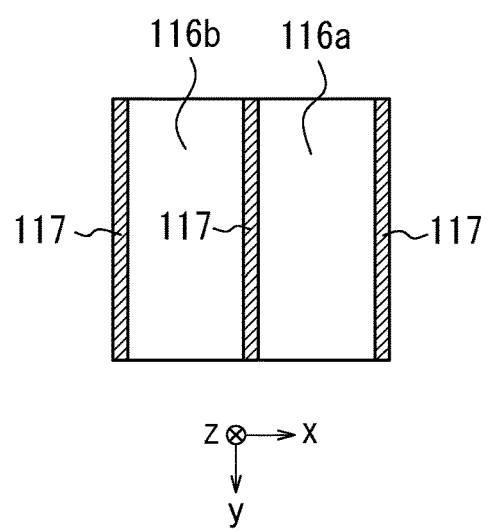
FIG. 2B is an expanded plan view of the pair of photodetectors in FIG. 2A.

FIG. 2A is a partially expanded cross-sectional diagram in the z-x plane of the camera portion 113. The microlens array 115 includes multiple microlenses 115a arranged two dimensionally in the x-axis direction and the y-axis direction. Light is blocked between adjacent microlenses 115a by a light-shielding wall 115b extending in the z-axis direction. The image pickup element 116 includes a pair of (i.e. two) photodetectors 116a and 116b corresponding to each microlens 115a. The photodetectors 116a and 116b are divided in the x-axis direction. A light-shielding film 117 is formed on the surface (light-receiving surface) of the image pickup element 116, extending in the y-axis direction between photodetectors that are adjacent in the x-axis direction. FIG. 2B is an expanded plan view from the z-axis direction illustrating the pair of photodetectors 116a and 116b.

In FIG. 1, the reflected illumination optical system 130 includes a light source (white light source) 131, a collector lens 132, a shutter 133, an aperture stop 134, a field lens 135, and a half mirror 136. The half mirror 136 is disposed at an inclination in the optical path of an observation optical system 100 between the objective lens 111 and the imaging lens 112. The illumination light emitted from the light source 131 passes through the collector lens 132, shutter 133, aperture stop 134, and field lens 135 and strikes the half mirror 136. The illumination light that strikes the half mirror 136 is reflected by the half mirror 136, passes through the objective lens 111, and illuminates the specimen 10.

The observation unit 100B is configured similarly to the observation unit 100A. Constituent elements that are identical to those of the observation unit 100A are labeled with the same reference signs, and a description thereof is omitted. In FIG. 1, the observation units 100A and 100B are disposed so that the optical axes of the respective objective lenses 111 nearly match.

The specimen 10 is supported by a support 11, such as a prepared slide, a petri dish, or the like that can be observed from both above and below. The support 11 is mounted on a microscope stage that can be observed from both above and below.

In the microscope apparatus according to this embodiment, upon the specimen 10 being illuminated by the illumination light from the light source 131 of the observation unit 100A, if the specimen 10 is a nearly transparent object, the illumination light is modulated by passing through the specimen 10 and is incident on the objective lens 111 of the observation unit 100B at the opposite side. The modulated light from the specimen 10 that is incident on the objective lens 111 of the observation unit 100B passes through the half mirror 136 of the observation unit 100B and forms an image of the specimen 10 on the camera portion 113 via the imaging lens 112. When the specimen 10 is an opaque object, the illumination light is modulated by being reflected and scattered by the specimen 10 and is incident on the objective lens 111 of the observation unit 100A. The illumination light then passes through the half mirror 136 of the observation unit 100A and forms an image of the specimen 10 on the camera portion 113 via the imaging lens 112.

Similarly, upon the specimen 10 being illuminated by the illumination light from the light source 131 of the observation unit 100B, if the specimen 10 is a nearly transparent object, the illumination light is modulated by passing through the specimen 10 and is incident on the objective lens 111 of the observation unit 100A at the opposite side. The modulated light from the specimen 10 that is incident on the objective lens 111 of the observation unit 100A passes through the half mirror 136 of the observation unit 100A and forms an image of the specimen 10 on the camera portion 113 via the imaging lens 112. When the specimen 10 is an opaque object, the illumination light is modulated by being reflected and scattered by the specimen 10 and is incident on the objective lens 111 of the observation unit 100B. The illumination light then passes through the half mirror 136 of the observation unit 100B and forms an image of the specimen 10 on the camera portion 113 via the imaging lens 112.

Based on output from the image pickup element 116 of the observation unit 100A, the image processor 200 measures the shape of the specimen 10 using the observation unit 100A. Similarly, based on output from the image pickup element 116 of the observation unit 100B, the image processor 200 measures the shape of the specimen 10 using the observation unit 100B. The image processor 200 then measures the overall shape of the specimen 10 from the results of the shape measurements using the observation units 100A and 100B.

Figure 3:
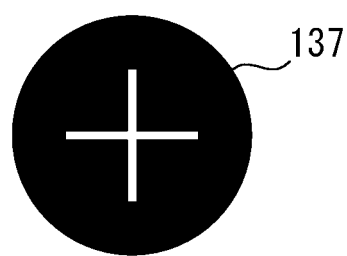
FIG. 3 is a plan view illustrating an example of the marker in FIG. 1.

In the microscope apparatus according to this embodiment, in order to measure the shape of the specimen 10 in the image processor 200, a common reference point for the observation units 100A and 100B is set as a reference for the distance in the optical axis direction (z-axis) and the position in the x-axis direction and the y-axis direction. Therefore, for example the reflected illumination optical system 130 of the observation unit 100A is configured to allow a marker 137 to be removable from the illumination light path between the aperture stop 134 and the field lens 135. The marker 137 for example has a cross shape, as illustrated in the plan view in FIG. 3 along the optical axis direction.

Figure 4:
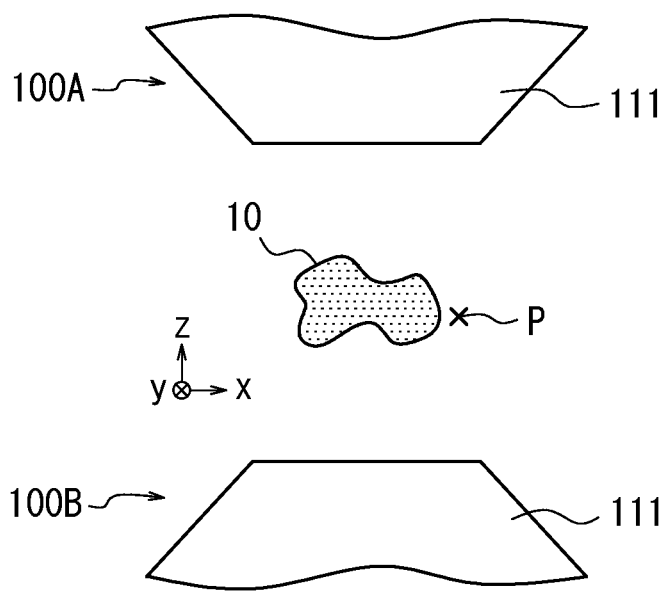
FIG. 4 illustrates the projection position of the marker.

By the marker 137 being inserted in the reflected illumination optical system 130 of the observation unit 100A before measuring the shape of the specimen 10, the marker image is projected by the objective lens 111 of the observation unit 100A onto the focal position at the object side of the objective lens 111. As illustrated in FIG. 4, by adjusting the position of the marker 137 in the optical axis direction, the projection position P of the marker image is preferably set to be close to the specimen 10, nearly in the middle of the thickness of the specimen 10 in the optical axis direction.

Once the marker image from the observation unit 100A is projected to a desired position, the observation unit 100B is focused on the marker image. As a result, the observation units 100A and 100B are each positioned on the focal position at the object side of the objective lens 111. The controller 300 sets and stores a reference point by taking the position, in the z-axis direction, of the objective lens 111 in each of the in-focus observation units 100A and 100B to be 0 (the same point) in the movement amount detector. The reference point may similarly be set with the marker 137 being removable from the reflected illumination optical system 130 of the observation unit 100B.

After the reference point is set, when measuring the shape of the specimen 10, the observation units 100A and 100B are first focused on the specimen 10. The controller 300 stores the value of the movement amount detector of each of the in-focus observation units 100A and 100B. Next, the controller 300 simultaneously images the specimen 10 with the observation units 100A and 100B. At this time, if a flare or the like occurs due to the illumination light, the controller 300 may control the shutter 133 in the reflected illumination optical systems 130 to switch instantaneously between the illumination light of the observation units 100A and 100B for sequential imaging. Subsequently, the controller 300 measures the shape of the specimen 10 based on a signal output from the image pickup element 116 of each of the observation units 100A and 100B by imaging the specimen 10.

In the camera portion 113 of each of the observation units 100A and 100B, the light-receiving surface of the image pickup element 116 is positioned at the focal position of the microlens array 115. Therefore, an image of the exit pupil of the objective lens 111 is formed on the light-receiving surface of the pair of photodetectors 116a and 116b corresponding to each microlens 115a. The image processor 200 calculates the parallax fir the image plane overall from the difference between the images acquired from the pair of photodetectors for each image pickup element 116. The image processor 200 then converts the resulting parallax into the distance Δz in the optical axis direction from the reference point using the following equation. As a result, the image processor 200 calculates a depth map (3D information) for the entire specimen 10 and completes shape measurement.

$$\Delta z = \frac{2x}{\beta \cdot NA}$$

where
β: magnification of objective lens
NA: numerical aperture of objective lens
x: amount of displacement from optical axis of ambient light beam on imaging plane With the microscope apparatus according to this embodiment, the specimen 10 is imaged from two directions, above and below, by the observation units 100A and 100B, and the shape of the specimen 10 is measured in terms of the relative distance from a reference point. Therefore, accurate stereoscopic shape information on the specimen 10 can be acquired rapidly.

Embodiment 2

Figure 5:
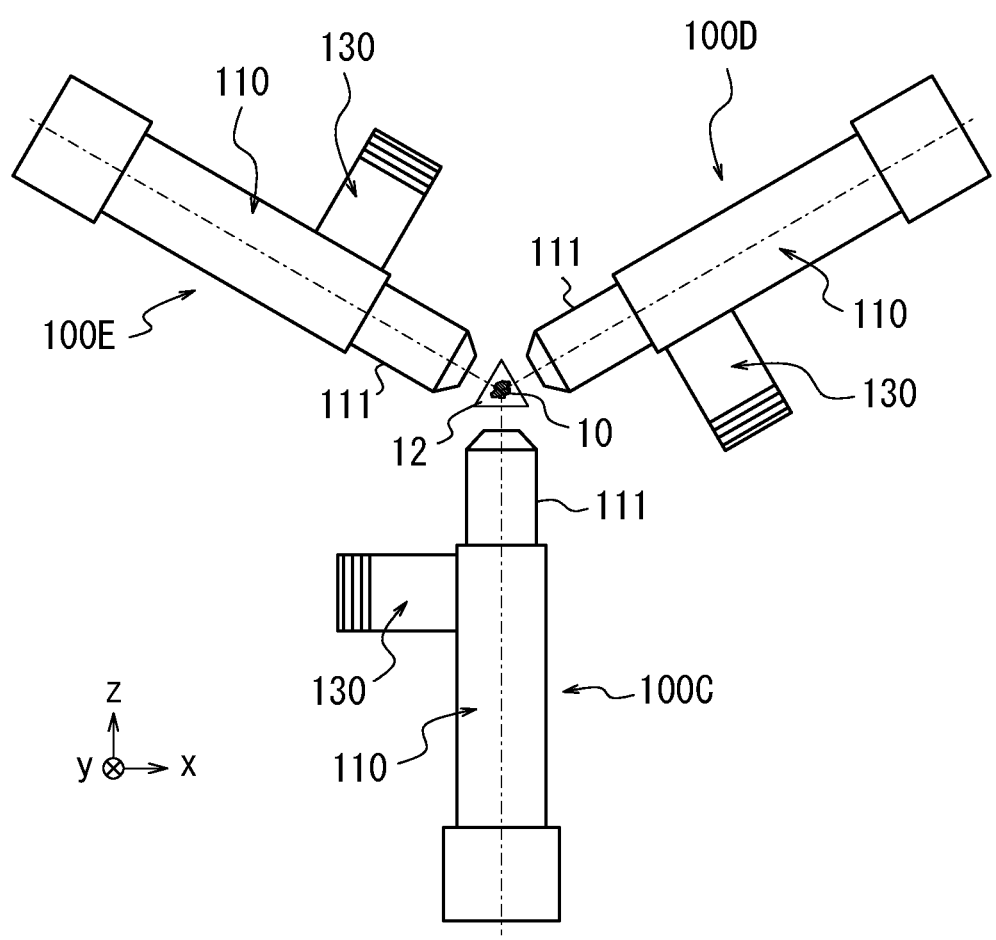
FIG. 5 is an external view schematically illustrating the main structure of a microscope apparatus as an image pickup apparatus according to Embodiment 2.

FIG. 5 is an external view schematically illustrating the main structure of a microscope apparatus as an image pickup apparatus according to Embodiment 2. The microscope apparatus according to this embodiment differs from Embodiment 1 by including three observation units 100C, 100D, and 100E that observe a specimen (object) 10 from below and in two diagonal directions from above, for a total of three directions.

Like the observation unit 100A in Embodiment 1, each of the observation units 100C, 100D, and 100E is configured to have an observation optical system 110 and a reflected illumination optical system 130, and the reflected illumination optical system 130 of at least one of the observation units (for example, the observation unit 100C) has the function of projecting a marker. The observation units 100C, 100D, and 100E can move along their respective optical axes and can focus on the specimen 10. The displacement amounts are read by the respective movement amount detectors and are stored in the controller 300 (see FIG. 1). In FIG. 5, for the sake of explanation, the optical axis direction of the observation unit 100C that observes the lower portion of the specimen 10 is defined as the z-axis direction; the direction within the page, orthogonal to the z-axis direction, is defined as the x-axis direction; and the direction perpendicular to the page, orthogonal to both the z-axis direction and the x-axis direction, is defined as the y-axis direction.

Along with liquid, the specimen 10 is inserted inside a support 12, which for example is a triangular prism made of transparent glass. The support 12 is disposed so that the faces of the triangular prism are respectively orthogonal to the optical axis directions of the observation units 100C, 100D, and 100E.

In the microscope apparatus according to this embodiment, for example the marker is projected from the observation unit 100C onto the surface of a portion of the specimen 10. Next, the observation units 100D and 100E are focused on the projected image of the marker. As a result, the observation units 100C, 100D, and 100E are each positioned on the focal position at the object side of the objective lens. The controller 300 sets and stores a reference point by taking the position, in the z-axis direction, of each of the in-focus observation units 100C, 100D, and 100E to be 0 (the same point) in the movement amount detector. Subsequently, in the same way as in Embodiment 1, the observation units 100C, 100D, and 100E are focused on the specimen 10 to image the specimen 10 simultaneously. The image processor 200 (see FIG. 1) then measures the overall shape of the specimen 10 based on a signal output from the image pickup element 116 (see FIG. 1) of each of the observation units 100C, 100D, and 100E by imaging the specimen 10.

With the microscope apparatus according to this embodiment, the specimen 10 is imaged from three directions by the observation units 100C, 100D, and 100E, and the shape of the specimen 10 is measured in terms of the relative distance from a reference point. Therefore, more accurate stereoscopic shape information on the specimen 10 can be acquired rapidly.

Embodiment 3

Figure 6:
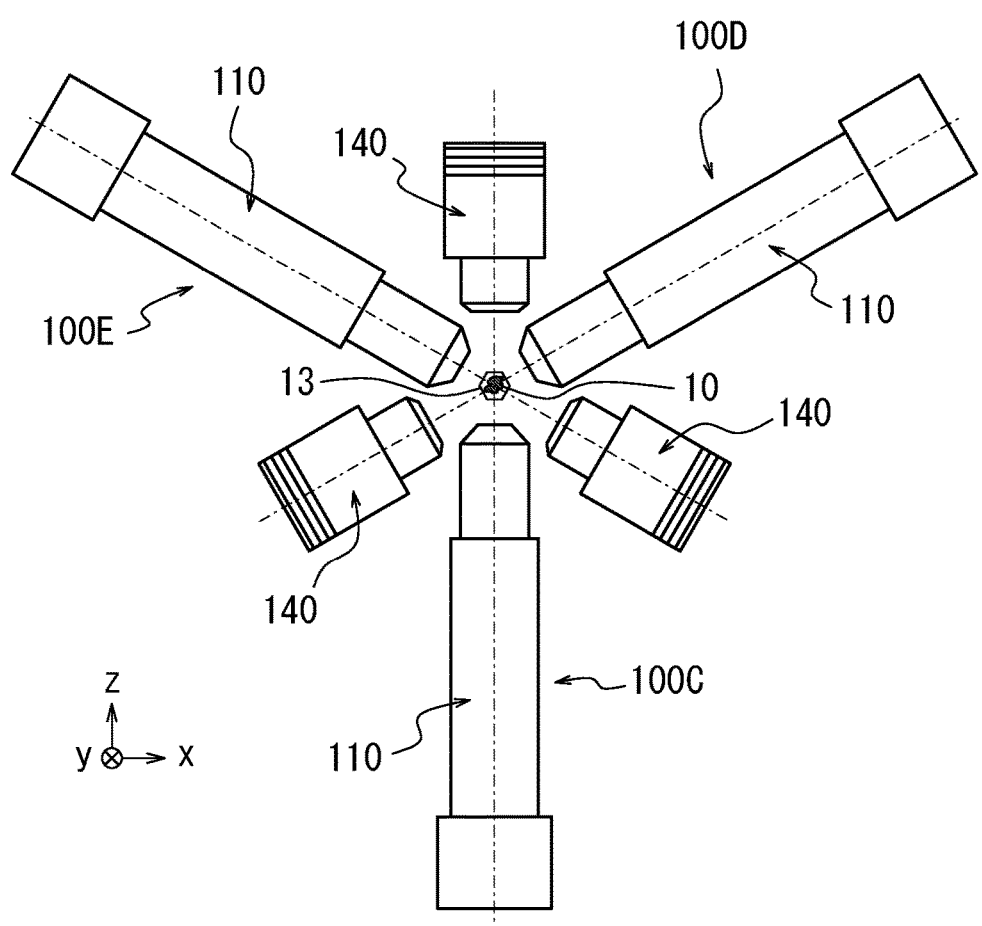
FIG. 6 is an external view schematically illustrating the main structure of a microscope apparatus as an image pickup apparatus according to Embodiment 3.

FIG. 6 is an external view schematically illustrating the main structure of a microscope apparatus as an image pickup apparatus according to Embodiment 3. The microscope apparatus according to this embodiment has the structure of the microscope apparatus according to Embodiment 2, except that the illumination optical systems of the observation units 100C, 100D, and 100E are configured as transmitted optical illumination systems 140 instead of reflected illumination optical systems 130 and are each disposed opposite the corresponding observation optical system 110 with the specimen 10 therebetween. The transmitted optical illumination systems 140 are configured by known optical elements that can switch between dark-field illumination and bright-field illumination, and a shutter may be inserted as necessary.

The observation optical system 110 of each of the observation units 100C, 100D, and 100E is configured to be moveable in the optical axis direction of the objective lens to allow focusing on the specimen 10. The displacement amount at this time is read by the movement amount detector and is stored in the controller 300 (see FIG. 1).

Figure 7:
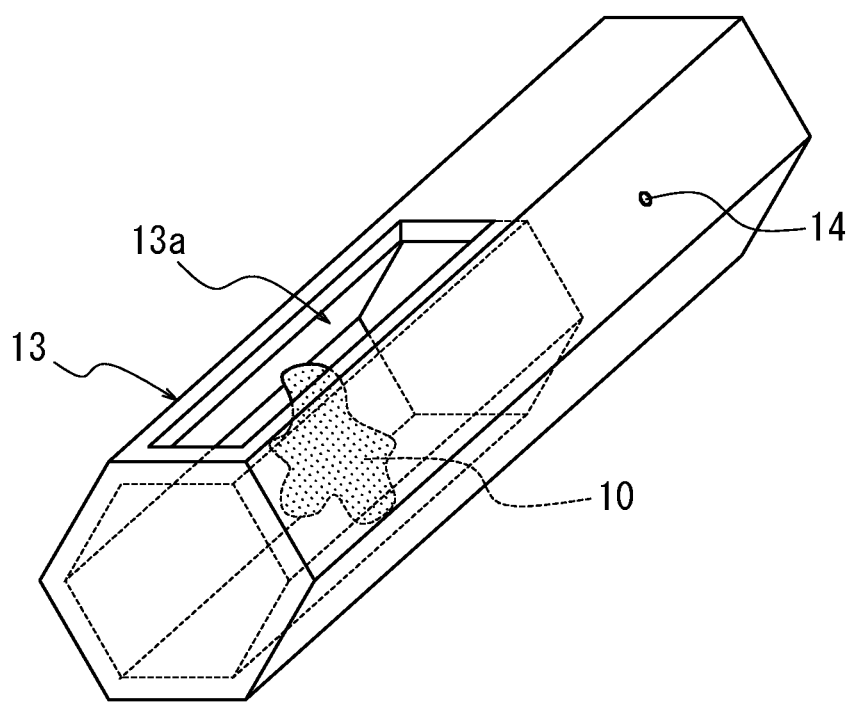
FIG. 7 is a perspective view schematically illustrating an example of the support in FIG. 6.
Figure 7:
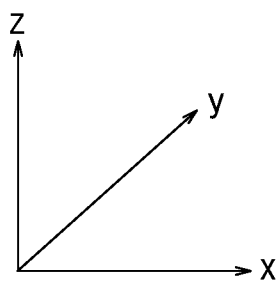

Along with liquid, the specimen 10 is stored in a container 13a formed at one end of a support 13, which is a hexagonal cylinder made from transparent glass, for example as schematically illustrated in the perspective view in FIG. 7. The other end of the support 13 is formed to be solid, and a minute scatterer 14, for example formed by spherical bubbles with a diameter of approximately 0.1 μm, is formed at nearly the center of the other end.

In the microscope apparatus according to this embodiment, first, the minute scatterer 14 of the support 13 is positioned at nearly the center of the field of view of the microscope observation area, and the minute scatterer 14 is subjected to dark-field illumination for example by the transmitted optical illumination system 140 corresponding to the observation unit 100C. The focal position at the object side of the observation optical system 110 corresponding to the transmitted optical illumination system 140 is matched to the minute scatterer 14, and the position of the observation optical system 110 in the optical axis direction at that time is read by the movement amount detector and is stored in the controller 300. Similarly, for the observation units 100D and 100E as well, the minute scatterer 14 is subjected to dark-field illumination by the corresponding transmitted optical illumination system 140, the focal position at the object side of each observation optical system 110 is matched to the minute scatterer 14, and the position in the optical axis direction at that time is read by the movement amount detector and is stored in the controller 300. The controller 300 then sets a reference point, taking the positions of the in-focus observation units 100C, 100D, and 100E in the optical axis direction to be 0 (the same point) in the movement amount detector.

Subsequently, the support 13 is slid in the x-y plane (the microscope stage), and the specimen 10 stored in the support 13 is positioned at nearly the center of the field of view of the microscope observation area. In the same way as in Embodiment 1, the specimen 10 is then subjected to bright-field illumination by the corresponding transmitted optical illumination systems 140, and the observation units 100C, 100D, and 100E are each focused on the specimen 10 to image the specimen 10 simultaneously. At this time, if a flare or the like occurs due to the illumination light, the controller 300 may control the shutter in the transmitted illumination optical systems 140 to switch instantaneously between the illumination light of the observation units 100C, 100D, and 100E for sequential imaging. The image processor 200 (see FIG. 1) then measures the overall shape of the specimen 10, in a way similar to Embodiment 1, based on a signal output from the image pickup element 116 (see FIG. 1) of each of the observation units 100C, 100D, and 100E by imaging the specimen 10.

With the microscope apparatus according to this embodiment, as in the case of Embodiment 2, more accurate stereoscopic shape information on the specimen 10 can be acquired rapidly. Furthermore, since the reference point is set with the minute scatterer 14 formed in the support 13 that supports the specimen 10, there is no need to project a marker for setting the reference point, thereby simplifying the configuration of the illumination optical system.

Embodiment 4

Figure 8A:
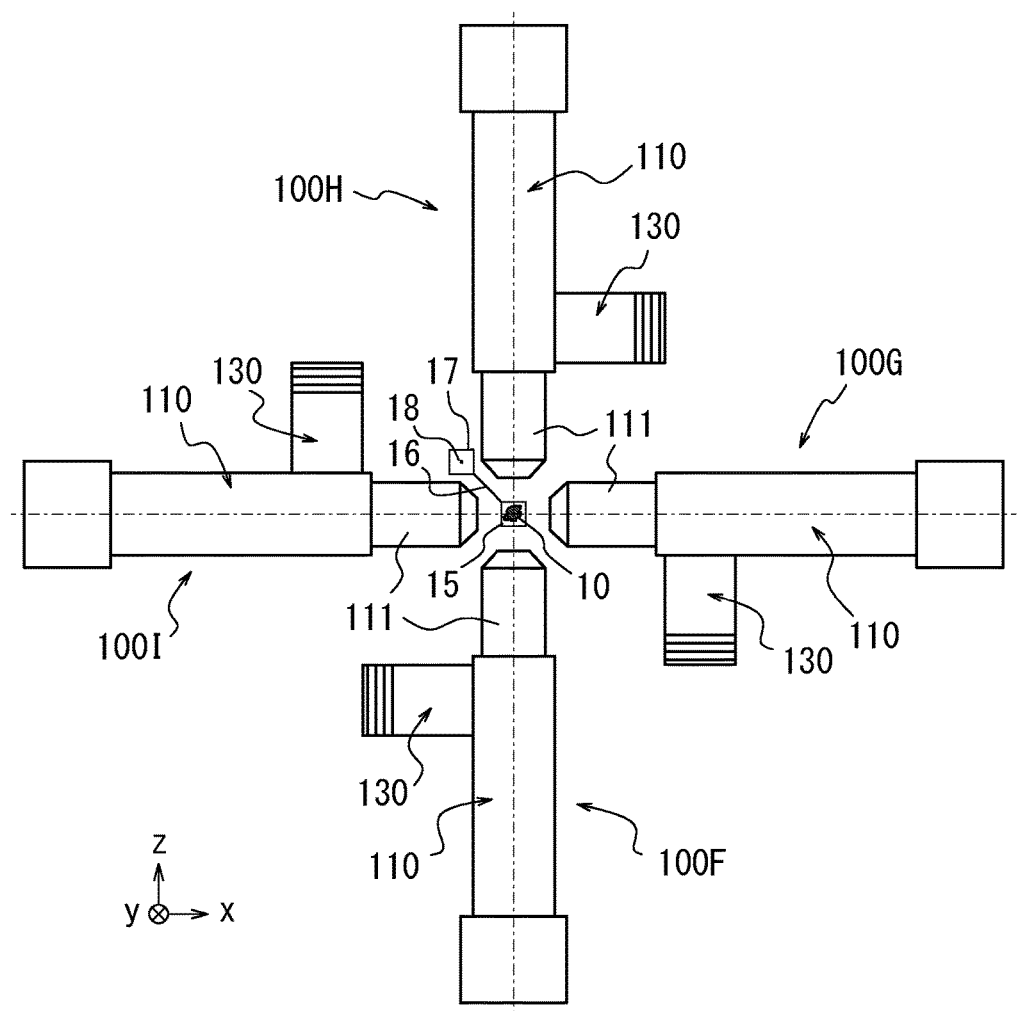
FIG. 8A is an external view schematically illustrating the main structure of a microscope apparatus as an image pickup apparatus according to Embodiment 4.
Figure 8B:
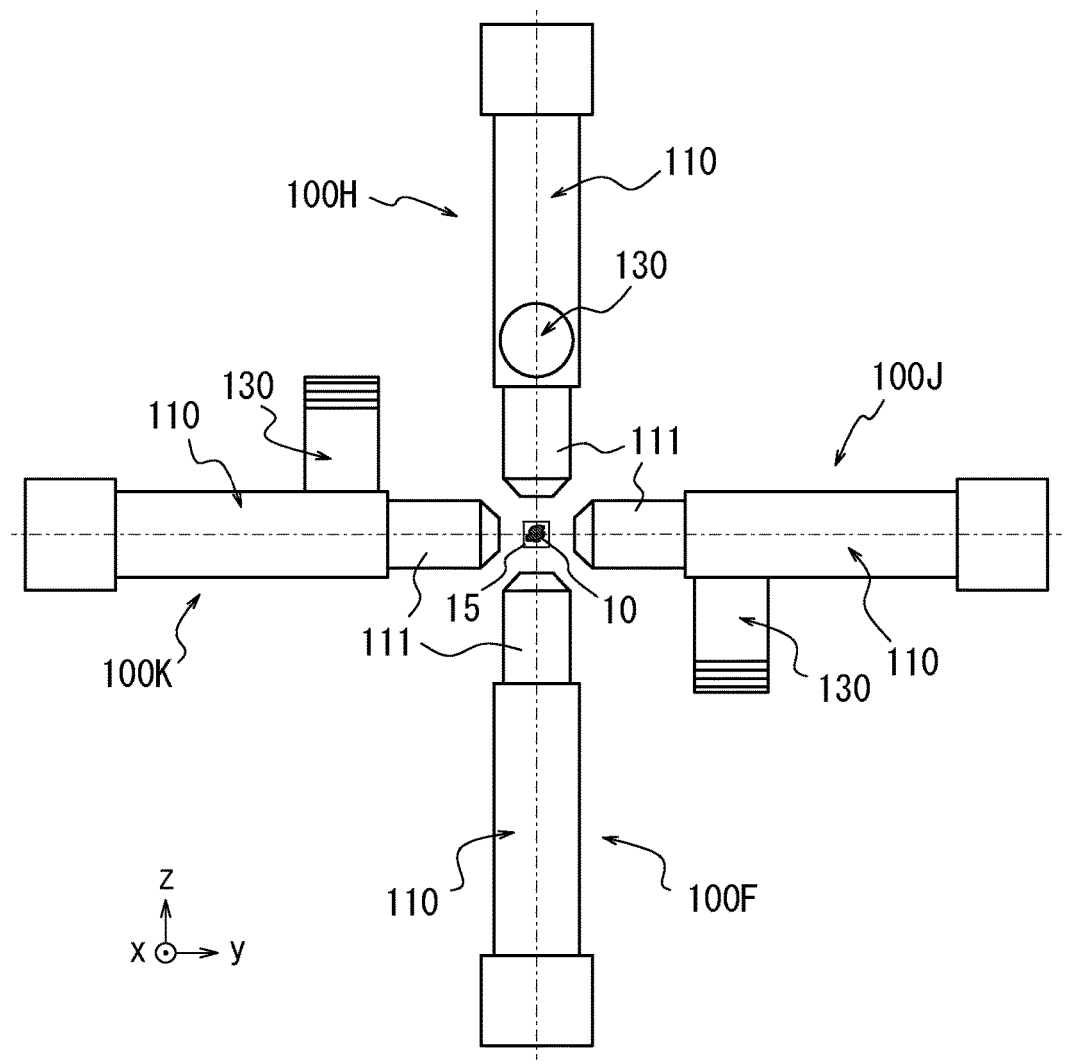
FIG. 8B is an external view schematically illustrating the main structure of a microscope apparatus as an image pickup apparatus according to Embodiment 4.

FIGS. 8A and 8B are external views schematically illustrating the main structure of a microscope apparatus as an image pickup apparatus according to Embodiment 4. The microscope apparatus according to this embodiment is provided with six observation units 100F to 100K that observe a specimen (object) 10 from six directions. Like the observation unit 100A in Embodiment 1, each of the observation units 100F to 100K includes an observation optical system 110 and a reflected illumination optical system 130. In this embodiment, however, none of the reflected illumination optical systems 130 has the function of projecting a marker.

The observation units 100F to 100K can move along their respective optical axes and can focus on the specimen 10. The displacement amounts are read by the respective movement amount detectors and are stored in the controller 300 (see FIG. 1). In FIG. 8A and FIG. 8B, for the sake of explanation, the optical axis direction of the observation unit 100F for observing the lower portion of the specimen 10 is defined as the z-axis direction, the direction orthogonal to the z-axis direction is defined as the x-axis direction, and the direction orthogonal to both the z-axis direction and the x-axis direction is defined as the y-axis direction. FIG. 8A illustrates arrangement of the observation units 100F to 100I in the z-x plane, and FIG. 8B illustrates arrangement of the observation units 100F, 100H, 100J, and 100K in the z-y plane.

Along with liquid, the specimen 10 is stored in a support 15, which for example is a cube made of transparent glass. A reference point setting member 17 formed by a cube of the same material and size as the support 15 is connected to the support 15 by a connector 16. The connector 16 is joined to any side of the support 15 and of the reference point setting member 17. A minute scatterer 18, for example formed by spherical bubbles with a diameter of approximately 0.1 μm, is formed at nearly the center of the reference point setting member 17, as in Embodiment 3. The support 15 and the reference point setting member 17 are slid to be selectively disposed at nearly the center of the field of view of the microscope observation area so that the sides of the cube are orthogonal to the optical axis directions of the observation units 100F to 100K.

In the microscope apparatus according to this embodiment, first, the minute scatterer 18 of the reference point setting member 17 is positioned at nearly the center of the field of view of the microscope observation area, and the minute scatterer 18 is subjected to dark-field illumination by the reflected illumination optical system 130 of one of the observation units 100F to 100K (for example, the observation unit 100F). In the state, the observation optical system 110 of the corresponding observation unit (for example, the observation unit 100H) is focused by matching the focal position at the object side of the observation optical system 110 to the minute scatterer 18, and the position of the observation optical system 110 in the optical axis direction at that time is read by the movement amount detector and is stored in the controller 300. Next, by dark-field illumination of the minute scatterer 18 by the reflected illumination optical system 130 of the observation unit 100H, the opposing observation unit 100F is similarly focused, and the position, in the optical axis direction, of the observation optical system 110 in the observation unit 100F at that time is read by the movement amount detector and is stored in the controller 300. By similarly focusing the other opposing observation units, the position in the optical axis direction at that time is read by the movement amount detector and is stored in the controller 300. The controller 300 then sets a reference point, taking the positions of the in-focus observation units 100F to 100K in the optical axis direction to be 0 (the same point) in the movement amount detector.

Subsequently, the support 15 and the reference point setting member 17 are slid in the x-y plane (the microscope stage), and the specimen 10 stored in the support 15 is positioned at nearly the center of the field of view of the microscope observation area. As in Embodiment 1, the specimen 10 is subjected to bright-field illumination by the reflected illumination optical systems 130 of the observation units 100F to 100K, and the observation units 100F to 100K are focused on the specimen 10 to image the specimen 10 simultaneously. The image processor 200 (see FIG. 1) then measures the overall shape of the specimen 10, in a way similar to Embodiment 1, based on a signal output from the image pickup element 116 (see FIG. 1) of each of the observation units 100F to 100K by imaging the specimen 10.

With the microscope apparatus according to this embodiment, the specimen 10 is imaged from six directions by the observation units 100F to 100K, and the shape of the specimen 10 is measured in terms of the relative distance from a reference point. Therefore, more accurate stereoscopic shape information on the specimen 10 can be acquired rapidly. Furthermore, there is no need to project a marker for setting the reference point, thereby simplifying the configuration of the illumination optical system.

Embodiment 5

Figure 9:
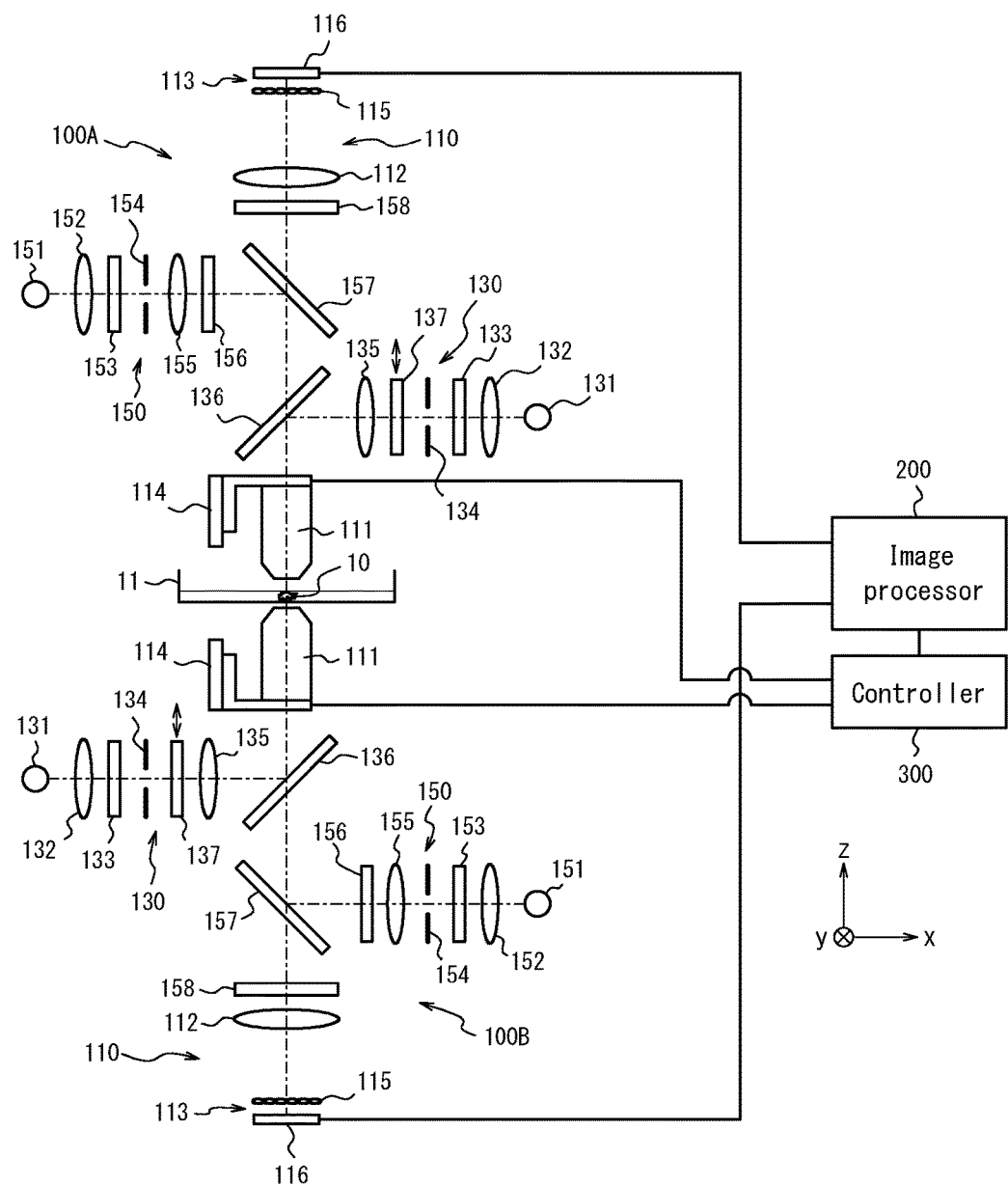
FIG. 9 schematically illustrates the main structure of a microscope apparatus as an image pickup apparatus according to Embodiment 5.

FIG. 9 schematically illustrates the main structure of a microscope apparatus as an image pickup apparatus according to Embodiment 5. The microscope apparatus according to this embodiment has the configuration of the microscope apparatus according to Embodiment 1, except that the fluorescent stereoscopic shape of the specimen 10 can also be measured. The differences from Embodiment 1 are described below.

In this embodiment, the observation units 100A and 100B are each provided with an excitation light illumination optical system 150. The excitation light illumination optical system 150 is provided with a light source tier excitation 151, a collector lens 152, a shutter 153, an aperture stop 154, a field lens 155, an excitation filter 156, and a dichroic mirror 157. Among light emitted from the light source for excitation 151, the excitation filter 156 transmits excitation light that causes the specimen 10 to undergo fluorescence emission. The dichroic mirror 157 is disposed at an inclination in the optical path of the observation optical system 100 between the objective lens 111 and the imaging lens 112, reflects the excitation light towards the objective lens 111, and transmits other light, such as the fluorescent light emitted by the specimen 10 and the illumination light from the light source 131. An absorption filter 158 that absorbs excitation light is also disposed in the observation optical system 100 on the object side of the imaging lens 112.

In this embodiment, as in Embodiment 1, a marker image is projected onto a desired position by the reflected illumination optical system 130 of the observation unit 100A, and the reference point of the observation units 100A and 100B is set. After setting the reference point, the excited light emitted from the light source for excitation 151 passes through the collector lens 152, the shutter 153, the aperture stop 154, the field lens 155, the excitation filter 156, the dichroic mirror 157, and the objective lens 111 and is irradiated onto the specimen 10. As a result, the specimen 10 emits fluorescent light. In this state, the observation units 100A and 100B are focused on the specimen 10, the values of the movement amount detector at that time are stored in the controller 300, and a fluorescent image of the specimen 10 is captured simultaneously. At this time, if a flare or the like occurs due to the excitation light, the controller 300 may control the shutter 153 in the excitation light illumination optical systems 150 to switch instantaneously between the excitation light of the observation units 100A and 100B for sequential capture of fluorescent images. Subsequently, the controller 300 measures the shape using fluorescent light of the specimen 10 based on a signal output from the image pickup element 116 of each of the observation units 100A and 100B by fluorescent imaging of the specimen 10.

With the microscope apparatus according to this embodiment, a fluorescent image of the specimen 10 is captured from two directions, above and below, by the observation units 100A and 100B, and the shape based on fluorescent light of the specimen 10 is measured in terms of the relative distance from a reference point. Therefore, accurate stereoscopic shape information on the specimen 10 based on fluorescent light can be acquired rapidly.

Embodiment 6

Figure 10:
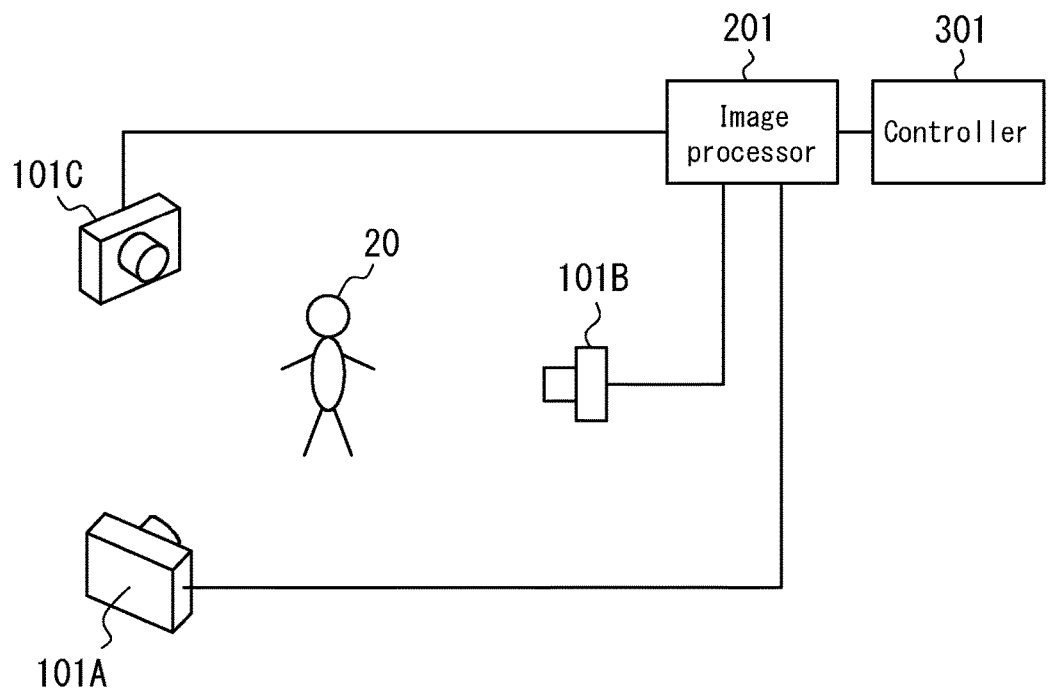
FIG. 10 schematically illustrates the main structure of an image pickup apparatus according to Embodiment 6.

FIG. 10 schematically illustrates the main structure of a microscope apparatus as an image pickup apparatus according to Embodiment 6. The image pickup apparatus according to this embodiment includes three cameras, namely cameras 101A, 101B, and 101C. Like the observation optical system 110 of the observation unit 100A in Embodiment 1, the cameras 101A, 101B, and 101C are each configured as light field cameras that include an objective lens and are connected to an image processor 201. The image processor 201 is connected to a controller 301 that controls overall operations of the image pickup apparatus.

In the image pickup apparatus according to this embodiment, the three cameras 101A, 101B, and 101C are focused on a subject 20, such as a specimen or a target object, and the subject 20 is simultaneously imaged. In the image processor 201, the distance to a point of the subject 20 appearing in both of the images captured by the cameras 101A and 101B is measured from a parallax image. Similarly, for cameras 101B and 101C and cameras 101C and 101A, the distance to a point of the subject 20 appearing in both of the captured images is measured from a parallax image. Based on the measured distances, the positional relationship of the three cameras 101A, 101B, and 101C, i.e. a reference point, is calculated in the image processor 201.

Next, depth maps indicating the relative distance from the reference point are created based on the parallax images captured by the three cameras 101A, 101B, and 101C. Subsequently, the three created depth maps are combined to calculate an overall depth map for the subject 20 (3D information), thereby measuring the overall shape of the subject 20.

With the image pickup apparatus according to this embodiment, the subject 20 is imaged from three directions by the three cameras 101A, 101B, and 101C, and the shape of the subject 20 is measured in terms of the relative distance from a reference point. Therefore, more accurate stereoscopic shape information on the subject 20 can be acquired rapidly.

Figure 11:
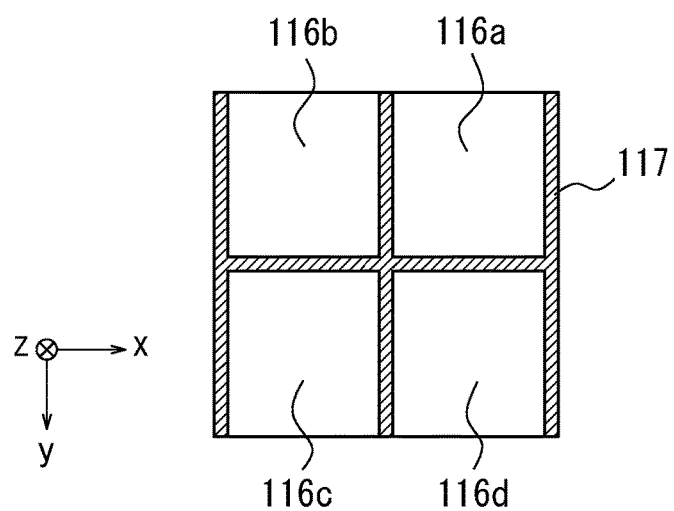
FIG. 11 illustrates a modification to the camera portion of FIG. 1.

This disclosure is not limited to the above embodiments, and a variety of changes and modifications may be made. For example, the specimen 10 is subjected to bright-field illumination in Embodiment 1 but may be subjected to dark-field illumination instead. In Embodiments 1 to 5, a wave plate may be inserted at the exit pupil of the objective lens of each observation unit to yield a phase-contrast microscope. As the image pickup element 116 in the camera portion 113 of FIG. 1, four photodetectors 116a to 116d separated in the x-axis direction and the y-axis direction, as illustrated in FIG. 11, may be disposed as the image pickup element 116 for one microlens in the microlens array 115, or an even greater number of photodetectors may be disposed.

Figure 12A:
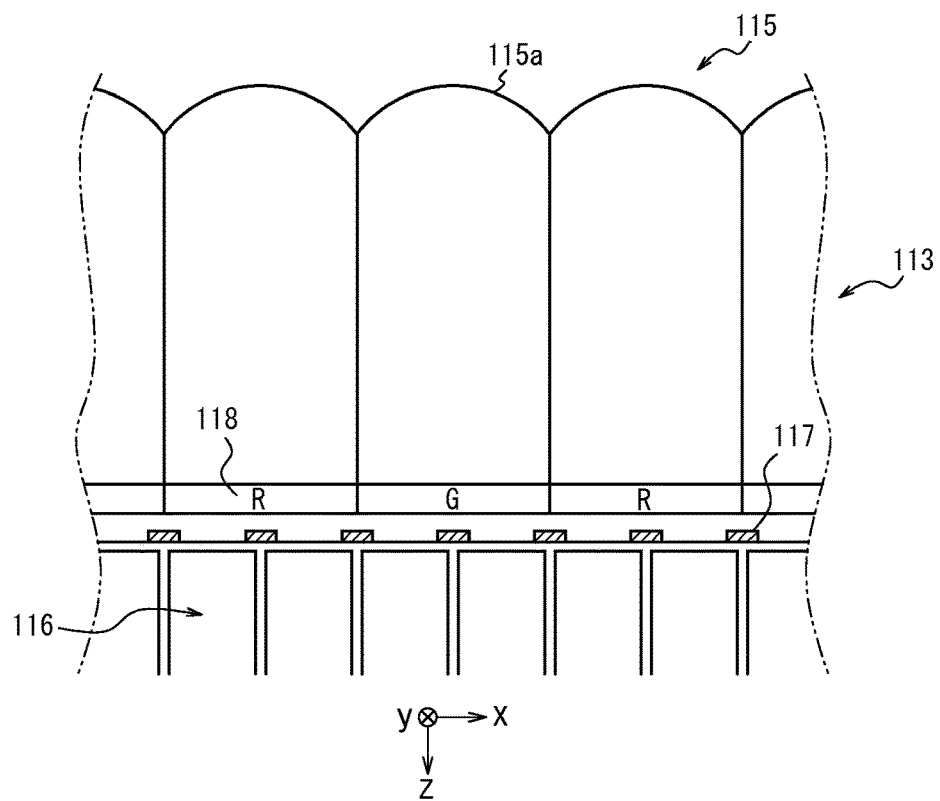
FIG. 12A illustrates another modification to the camera portion of FIG. 1.
Figure 12B:
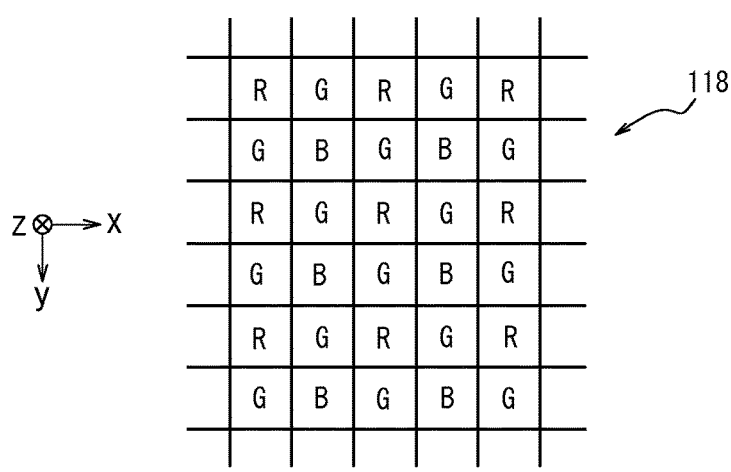
FIG. 12B illustrates an example arrangement of the color filters in FIG. 12A.

Furthermore, the camera portion 113 illustrated in FIG. 1 may obtain stereoscopic shape information in color by, for example, disposing an RGB color filter 118 between the microlens array 115 and the image pickup element 116, as illustrated in FIG. 12A, so that one color corresponds to one microlens 115a. In this case, the color filter 118 may, for example, be in a Bayer arrangement as illustrated in FIG. 12B or in another well-known arrangement.

Figure 13:
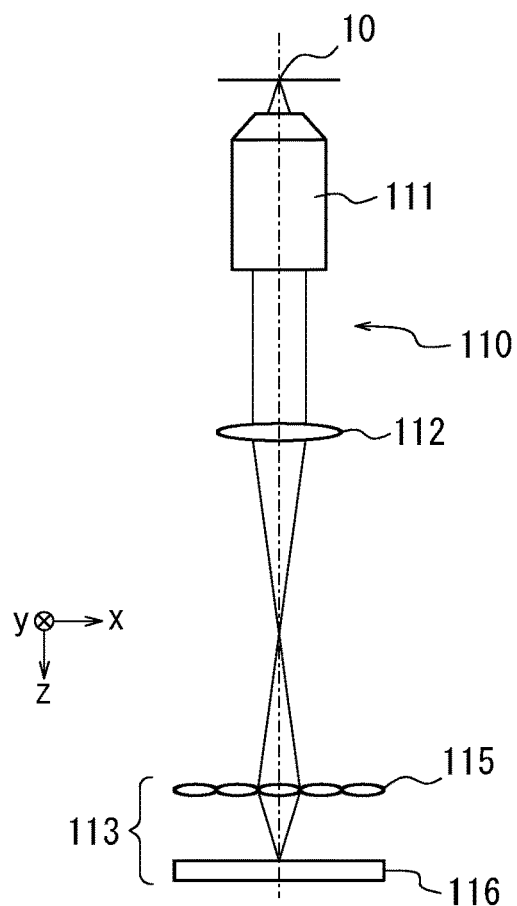
FIG. 13 illustrates yet another modification to the camera portion of FIG. 1.

The case of the microlens array 115 and the image pickup element 116 being in a Plenoptic 1.0 type arrangement in the camera portion 113 has been illustrated, but this example is not limiting. For example, similar shape measurement is also possible with a so-called Plenoptic 2.0 type arrangement, in which as illustrated in FIG. 13, the microlens array 115 and the image pickup element 116 are disposed so that the image formed by the imaging lens 112 is formed again on the image pickup element 116 by the microlens array 115.

Figure 14:
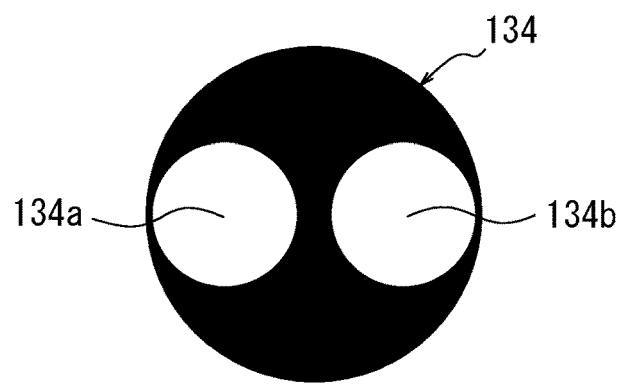
FIG. 14 illustrates a modification to the aperture stop of FIG. 1.

Furthermore, the aperture stop 134 of the reflected illumination optical system 130 illustrated in FIG. 1 may be configured to include two light transmission portions 134a and 134b that are symmetrical about the optical axis, for example as illustrated in FIG. 14. The aperture stop of the illumination optical systems 140 in FIG. 6 and the aperture stop 154 of the excitation light illumination optical systems 150 in FIG. 9 may also be configured in the same way as FIG. 14. The marker for setting the reference point in Embodiment 1, Embodiment 2, and Embodiment 5 may be projected by an independent projection optical system. In Embodiments 2 to 4 as well, the fluorescent stereoscopic shape of the specimen 10 can be measured by providing an excitation light illumination optical system as in Embodiment 5.

The image processor and the controller are provided separately in the above-described embodiments, but the image processor and the controller may be configured integrally.

The invention claimed is:

1. An image pickup apparatus comprising:
   a plurality of observation units configured to observe a specimen from different directions; and
   an image processor;
   wherein:
   each of the plurality of observation units comprises an objective lens, a lens array, and an image pickup element, receives incident light with the image pickup element, the lens array being disposed on a side of the image pickup element and at a formation position of an image of the specimen, the image pickup element being disposed at a focal position of the lens array, the incident light being modulated by the specimen and passing through the objective lens and the lens array, and outputs a plurality of image signals having a phase difference; and
   wherein the image processor measures a shape of the specimen in terms of relative distance from a predetermined reference point based on the image signals having a phase difference which are output from the plurality of observation units.

2. The image pickup apparatus of claim 1, wherein the image pickup element is disposed at a position where the image of the specimen is formed again by the lens array.

3. The image pickup apparatus of claim 1, wherein for each of the plurality of observation units, a focal position on a specimen side of the objective lens is positioned at the reference point.

4. The image pickup apparatus of claim 3, further comprising a projector configured to project a marker that becomes the reference point.

5. The image pickup apparatus of claim 4, wherein the projector projects the marker through the objective lens of one observation unit among the plurality of observation units onto the focal position on the specimen side of the objective lens.

6. The image pickup apparatus of claim 1, wherein the reference point is set using a scatterer disposed in an observation area.

7. The image pickup apparatus of claim 1, wherein the plurality of observation units measure the shape by fluorescent observation of the specimen.

* * * * *